US011021763B2

(12) United States Patent
Toolsie et al.

(10) Patent No.: US 11,021,763 B2
(45) Date of Patent: Jun. 1, 2021

(54) ASSAY FOR DETECTING HEPATITIS C VIRUS (HCV)

(71) Applicant: ABBOTT MOLECULAR INC., Des Plaines, IL (US)

(72) Inventors: Dan Toolsie, Des Plaines, IL (US); Shihai Huang, Des Plaines, IL (US); Hong Su, Des Plaines, IL (US); Darren Drapp, Des Plaines, IL (US); William Caminiti, Des Plaines, IL (US); Kara Nordin, Des Plaines, IL (US); Sevim Arslan, Des Plaines, IL (US); Sara Jones, Des Plaines, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 243 days.

(21) Appl. No.: 16/150,815

(22) Filed: Oct. 3, 2018

(65) Prior Publication Data

US 2019/0100813 A1    Apr. 4, 2019

Related U.S. Application Data

(60) Provisional application No. 62/567,630, filed on Oct. 3, 2017.

(51) Int. Cl.
*C12Q 1/68* (2018.01)
*C12Q 1/70* (2006.01)

(52) U.S. Cl.
CPC ......... *C12Q 1/707* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| 5,677,124 A | 10/1997 | Dubois et al. |
| 5,919,625 A | 7/1999 | Dubois et al. |
| 5,939,262 A | 8/1999 | Pasloske et al. |
| 6,623,919 B1 | 9/2003 | Gorman et al. |
| 2008/0299568 A1 | 12/2008 | Johnson et al. |
| 2014/0134611 A1 | 5/2014 | Bergmann et al. |

FOREIGN PATENT DOCUMENTS

| EP | 1746171 | 1/2007 |
| EP | 2392589 | 12/2011 |
| EP | 2722397 A1 | 4/2014 |
| WO | WO 2004011612 A2 | 2/2004 |
| WO | WO 2008134374 A1 | 11/2008 |
| WO | WO 2010078291 A1 | 7/2010 |
| WO | WO 2017011565 A1 | 1/2017 |

OTHER PUBLICATIONS

Abbott RealTime HCV Assay (CE); package insert No. 51-602124/R9, May 2015.
Abbott RealTime HCV Assay (FDA); package insert No. 51-608374/R4, Oct. 2014.
Bai et al., "Hepatitis C virus 3∝UTR regulates viral translation through direct interactions with the host translation machinery" Nucleic Acids Res., Sep. 2013, 41(16): 7861-7874.
Cepheid Gene Xpert HCV Assay (CE); package insert No. 301-3019, Rev. B, Mar. 2015.
Clarke B., "Molecular virology of hepatitis C virus" J. Gen. Virol., Oct. 1997, 78(10): 2397-410.
Dubuisson, J., "Hepatitis C virus proteins" World J. Gastroenterol, May 7, 2007, 13(17): 2406-15.
Echeverria et al., "Hepatitis C virus genetic variability and evolution" World J. Hepatol., Apr. 28, 2015, 7(6): 831-845.
Engle et al., "Development of a TaqMan assay for the six major genotypes of hepatitis C virus: comparison with commercial assays." J Med Virol. Jan. 2008; 80(1):72-9.
Halfon et al., "Real-time PCR assays for hepatitis C virus (HCV) RNA quantitation are adequate for clinical management of patients with chronic HCV infection." J Clin Microbiol. Jul. 2006; 44(7):2507-11.
Hologic Aptima HCV Quant Assay (US); Package insert No. AW-14498 Rev. 001, 2017.
Hologic Aptima HCV Quant Dx Assay (CE); package insert AW-13249-001 Rev. 001, 2015.
Hopf et al., "Long-term follow-up of posttransfusion and sporadic chronic hepatitis non-A, non-B and frequency of circulating antibodies to hepatitis C virus (HCV)" Hepatology, Jan. 1990, 10(1): 69-76.
Jove et al., "Post-transfusional vs. sporadic non-A, non-B chronic hepatitis. A clinicopathological and evolutive study" Liver, Feb. 1988, 8(1): 42-47.
Kim et al., "Validation of One-Step Real-Time RT-PCR Assay in Combination with Automated RNA Extraction for Rapid Detection and Quantitation of Hepatitis C Virus RNA for Routine Testing in Clinical Specimens." J. Microbiol. Biotechnol. (2005), 15(3): 595-602.
Miller & Purcell., "Hepatitis C virus shares amino acid sequence similarity with pestiviruses and flaviviruses as well as members of two plant virus supergroups" PNAS, Mar. 1, 1990, 87 (6): 2057-2061.
Pasloske et al., "Armored RNA technology for production of ribonuclease-resistant viral RNA controls and standards" J. Clin. Microbiol., Dec. 1998, 36(12): 3590-3594.
Roche cobas HCV 4800 Assay (CE); package insert No. 07529716001-02EN Doc. Rev.1.0, Aug. 2015.
Roche cobas HCV 6800/8800 Assay (CE); package insert No. 07175400001-01EN Doc. Rev. 1.0, Apr. 2016.
Roche cobas HCV 6800/8800 Assay (US); package insert No. 071754180001-01EN Doc.Rev. 1.0, 2015.

(Continued)

*Primary Examiner* — Stephanie K Mummert
(74) *Attorney, Agent, or Firm* — Casimir Jones, S.C.; Melissa Karabinis

(57) ABSTRACT

The disclosure is directed to methods, kits, and compositions, for amplifying and detecting a human hepatitis C virus (HCV) in a sample, which comprises a variety of combinations of forward oligonucleotide primers, reverse oligonucleotide primers, and oligonucleotide probes.

19 Claims, No Drawings
Specification includes a Sequence Listing.

(56) References Cited

OTHER PUBLICATIONS

Shi et al., "Involvement of the 3' Untranslated Region in Encapsidation of the Hepatitis C Virus" PLoS Pathog., Feb. 11, 2016, 12(2): 1-20.
Weiner A. J. et al., "Variable and Hypervariable Domains Are Found in the Regions of HCV Corresponding to the Flavivirus Envelope and NS1 Proteins and the Pestivirus Envelope Glycoproteins" Virology, Oct. 18, 1990, 180: 842.
Zitzer et al., "Second-generation Cobas AmpliPrep/Cobas TaqMan HCV quantitative test for viral load monitoring: a novel dual-probe assay design." J Clin Microbiol. Feb. 2013; 51(2):571-7.
International Search Report & Written Opinion dated Jan. 3, 2019, Intl. Appl. No. PCT/US2018/054161, 18 pages.

SEQUENCE LISTING

```
<160> NUMBER OF SEQ ID NOS: 26

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
atttgggcgt gccccgcaa ga                                                 22

<210> SEQ ID NO 2
<211> LENGTH: 26
<212> TYPE: DNA
<213> ORGANISM: Artificial Sequence
<220> FEATURE:
<223> OTHER INFORMATION: Synthetic

<400> SEQUENCE: 2
cccggggcac tcgcaagcac cctatc                                            26

<210> SEQ ID NO 3
<211> LENGTH: 17
<212> TYPE: DNA
<213> ORGANISM: Artificial Sequence
<220> FEATURE:
<223> OTHER INFORMATION: Synthetic

<400> SEQUENCE: 3
ccuuguggua cugccug                                                      17
```

```
<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
ctagccgagt agtgttgg                                                 18

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
atttgggcgt gcccccgcga ga                                            22

<210> SEQ ID NO 6
<211> LENGTH: 26
<212> TYPE: DNA
<213> ORGANISM: Artificial Sequence
<220> FEATURE:
<223> OTHER INFORMATION: Synthetic

<400> SEQUENCE: 6
cccggggcac tcgtaagcac cctatc                                        26

<210> SEQ ID NO 7
<211> LENGTH: 26
<212> TYPE: DNA
<213> ORGANISM: Artificial Sequence
<220> FEATURE:
<223> OTHER INFORMATION: Synthetic

<400> SEQUENCE: 7
cccgaggcac tcgcaagcac cctatc                                        26

<210> SEQ ID NO 8
<211> LENGTH: 26
<212> TYPE: DNA
<213> ORGANISM: Artificial Sequence
<220> FEATURE:
<223> OTHER INFORMATION: Synthetic

<400> SEQUENCE: 8
cccgaggcac tcgtaagcac cctatc                                        26

<210> SEQ ID NO 9
<211> LENGTH: 26
<212> TYPE: DNA
<213> ORGANISM: Artificial Sequence
<220> FEATURE:
<223> OTHER INFORMATION: Synthetic

<400> SEQUENCE: 9
cccggggcac tcgaaagcac cctatc                                        26

<210> SEQ ID NO 10
<211> LENGTH: 18
<212> TYPE: DNA
<213> ORGANISM: Artificial Sequence
<220> FEATURE:
```

```
<223> OTHER INFORMATION: Synthetic

<400> SEQUENCE: 10
ccttgtggta ctgcctga                                                 18

<210> SEQ ID NO 11
<211> LENGTH: 17
<212> TYPE: DNA
<213> ORGANISM: Artificial Sequence
<220> FEATURE:
<223> OTHER INFORMATION: Synthetic

<400> SEQUENCE: 11
ccuugtggta cugccug                                                  17

<210> SEQ ID NO 12
<211> LENGTH: 17
<212> TYPE: DNA
<213> ORGANISM: Artificial Sequence
<220> FEATURE:
<223> OTHER INFORMATION: Synthetic

<400> SEQUENCE: 12
ccuugtggua cugccug                                                  17

<210> SEQ ID NO 13
<211> LENGTH: 18
<212> TYPE: DNA
<213> ORGANISM: Artificial Sequence
<220> FEATURE:
<223> OTHER INFORMATION: Synthetic

<400> SEQUENCE: 13
ctagccgagt agtgttgg                                                 18

<210> SEQ ID NO 14
<211> LENGTH: 18
<212> TYPE: DNA
<213> ORGANISM: Artificial Sequence
<220> FEATURE:
<223> OTHER INFORMATION: Synthetic

<400> SEQUENCE: 14
cuagccgagu agtguugg                                                 18

<210> SEQ ID NO 15
<211> LENGTH: 28
<212> TYPE: DNA
<213> ORGANISM: Artificial Sequence
<220> FEATURE:
<223> OTHER INFORMATION: Synthetic

<400> SEQUENCE: 15
ctacagcaga gttggcagct tcactttc                                      28

<210> SEQ ID NO 16
<211> LENGTH: 22
<212> TYPE: DNA
<213> ORGANISM: Artificial Sequence
<220> FEATURE:
<223> OTHER INFORMATION: Synthetic

<400> SEQUENCE: 16
gtctggcctt tcagcaagtt tc                                            22
```

```
<210> SEQ ID NO 17
<211> LENGTH: 24
<212> TYPE: DNA
<213> ORGANISM: Artificial Sequence
<220> FEATURE:
<223> OTHER INFORMATION: Synthetic

<400> SEQUENCE: 17
acgagttcat gagggcaggc cgct                                          24

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
gctccatctt agccctagtc                                               20

<210> SEQ ID NO 19
<211> LENGTH: 26
<212> TYPE: DNA
<213> ORGANISM: Artificial Sequence
<220> FEATURE:
<223> OTHER INFORMATION: Synthetic

<400> SEQUENCE: 19
agcactctct gcagtcatgc ggctca                                        26

<210> SEQ ID NO 20
<211> LENGTH: 19
<212> TYPE: DNA
<213> ORGANISM: Artificial Sequence
<220> FEATURE:
<223> OTHER INFORMATION: Synthetic

<400> SEQUENCE: 20
cggctagctg tgaaaggtc                                                19

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
cggctagctg tgaaaggtcc g                                             21

<210> SEQ ID NO 22
<211> LENGTH: 17
<212> TYPE: DNA
<213> ORGANISM: Artificial Sequence
<220> FEATURE:
<223> OTHER INFORMATION: Synthetic

<400> SEQUENCE: 22
ccuuguggua cugccug                                                  17

<210> SEQ ID NO 23
<211> LENGTH: 17
<212> TYPE: DNA
<213> ORGANISM: Artificial Sequence
<220> FEATURE:
<223> OTHER INFORMATION: Synthetic
```

```
<400> SEQUENCE: 23
ccuugtggta cugccug                                              17

<210> SEQ ID NO 24
<211> LENGTH: 17
<212> TYPE: DNA
<213> ORGANISM: Artificial Sequence
<220> FEATURE:
<223> OTHER INFORMATION: Synthetic

<400> SEQUENCE: 24
ccuugtggua cugccug                                              17

<210> SEQ ID NO 25
<211> LENGTH: 18
<212> TYPE: DNA
<213> ORGANISM: Artificial Sequence
<220> FEATURE:
<223> OTHER INFORMATION: Synthetic

<400> SEQUENCE: 25
ctagccgagt agtgttgg                                             18

<210> SEQ ID NO 26
<211> LENGTH: 18
<212> TYPE: DNA
<213> ORGANISM: Artificial Sequence
<220> FEATURE:
<223> OTHER INFORMATION: Synthetic

<400> SEQUENCE: 26
cuagccgagu agtguugg                                             18
```

ASSAY FOR DETECTING HEPATITIS C VIRUS (HCV)

CROSS-REFERENCE TO RELATED APPLICATIONS

This application claims the benefit of U.S. Provisional Patent Application No. 62/567,630, filed Oct. 3, 2017, which is incorporated by reference herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 4,968 Byte ASCII (Text) file named "36071US2ORD_ST25.txt," created on Oct. 3, 2018.

BACKGROUND OF THE INVENTION

Hepatitis C Virus (HCV) is now recognized as being the primary cause of transfusion-associated non-A, non-B (NANB) hepatitis. HCV is a single-stranded, positive sense RNA virus with similarities to flaviviruses and pestiviruses (Miller R. H. and Purcell R. H., *Proc. Natl. Acad. Sci.*, 87: 2057 (1991); and Weiner A. J., et al., *Virology*, 180: 842 (1990)). Globally, an estimated 71 million people have chronic hepatitis C infection (World Health Organization, Hepatitis C Fact Sheet, July 2017).

Although the acute presentation of HCV is generally mild, with only 25% of patients developing jaundice, a large proportion (>50%) of infected individuals go on to develop chronic hepatitis with serious and potentially life threatening sequelae such as cirrhosis and hepatocellular carcinoma (Jove et al., *Liver*, 8: 42 (1990); and Hopf et al., *Hepatology*, 10: 69 (1990)). Approximately 399,000 people die each year from hepatitis C, mostly from cirrhosis and hepatocellular carcinoma (World Health Organization, Hepatitis C Fact Sheet, July 2017).

Infection with HCV is currently diagnosed by detection of anti-HCV antibodies (generally to the HCV structural core protein or non-structural NS3 protein) followed by direct detection of viral RNA by PCR. Many existing nucleic acid tests (NATs) for HCV utilize a single probe to detect and quantify HCV RNA. Such single-probe detection methods can result in underquantification or lack of detection of some rare HCV variants and emerging variants due to mutations within the probe region. Nucleic acid tests also are typically performed using PCR reagents provided in liquid format that require frozen storage and batch testing, and turn around-time for sample preparation and real-time PCR can exceed several hours for some tests. NAT also is prone to handling errors such as contamination, and RNA levels can drop below the limit of detection when the initial peak of virus resolves.

Thus, there remains a need for HCV detection methods and systems that (i) reliably detect all six HCV genotypes, (ii) are provided in a format that eliminates or reduces storage requirements and PCR reagent waste, and (iii) may be performed quickly. The present disclosure provides such methods and systems.

BRIEF SUMMARY OF THE INVENTION

The present disclosure provides a set of oligonucleotide sequences for amplifying and detecting a human hepatitis C virus (HCV) nucleic acid sequence in a sample, which comprises: (a) a forward primer oligonucleotide sequence comprising SEQ ID NO: 1 or SEQ ID NO: 5; (b) a reverse primer oligonucleotide sequence comprising SEQ ID NO: 2, SEQ ID NO: 6, SEQ ID NO: 7, SEQ ID NO: 8, or SEQ ID NO: 9; (c) a first probe oligonucleotide sequence comprising SEQ ID NO: 3, SEQ ID NO: 10, SEQ ID NO: 11, or SEQ ID NO: 12; and (d) a second probe oligonucleotide sequence comprising SEQ ID NO: 4, SEQ ID NO: 13, or SEQ ID NO: 14, wherein each of the first and second probe oligonucleotide sequences comprises a detectable label. Also provided is a method for detecting human HCV in a sample using the aforementioned set of oligonucleotides.

The present disclosure also provides a kit for detecting human hepatitis C virus (HCV) in a sample comprising: (a) a forward primer oligonucleotide sequence comprising SEQ ID NO: 1; (b) a reverse primer oligonucleotide sequence comprising SEQ ID NO: 2; (c) a first probe oligonucleotide sequence comprising SEQ ID NO: 3; (d) a second probe oligonucleotide sequence comprising SEQ ID NO: 4; (e) reagents for amplifying and detecting nucleic acid sequences; and (f) instructions for use, wherein each of the first and second probe oligonucleotide sequences comprises a detectable label.

The present disclosure further provides a composition comprising oligonucleotide sequences for amplifying and detecting a human hepatitis C virus (HCV) in a sample, which comprises: (a) a forward primer oligonucleotide sequence comprising SEQ ID NO: 1 or SEQ ID NO: 5; (b) a reverse primer oligonucleotide sequence comprising SEQ ID NO: 2, SEQ ID NO: 6, SEQ ID NO: 7, SEQ ID NO: 8, or SEQ ID NO: 9; (c) a first probe oligonucleotide sequence comprising SEQ ID NO: 3, SEQ ID NO: 10, SEQ ID NO: 11, or SEQ ID NO: 12; and (d) a second probe oligonucleotide sequence comprising SEQ ID NO: 4, SEQ ID NO: 13, or SEQ ID NO: 14, wherein each of the first and second probe oligonucleotide sequences comprises a detectable label.

DETAILED DESCRIPTION OF THE INVENTION

The present disclosure provides a set of oligonucleotides for amplifying and detecting human hepatitis C virus (HCV) in a sample. The term "oligonucleotide," as used herein, refers to a short nucleic acid sequence comprising from about 2 to about 100 nucleotides (e.g., about 5, 10, 15, 20, 25, 30, 35, 40, 45, 50, 55, 60, 65, 70, 75, 80, 85, 90, 95, 99, or 100 nucleotides, or a range defined by any of the foregoing values). The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, for example, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

Oligonucleotides can be single-stranded or double-stranded, or can contain portions of both double-stranded and single-stranded sequences. The oligonucleotide can be DNA, both genomic and complimentary DNA (cDNA), RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Oligonucleotides can be obtained by chemical synthesis methods or by recombinant methods. A particular oligonucleotide sequence can encompass conservatively modified variants thereof (e.g., codon substitutions), alleles, orthologs, single nucleotide polymorphisms (SNPs), and complementary sequences as well as the sequence explicitly indicated.

Primer and Probe Oligonucleotides

Oligonucleotides are used in a variety of applications in biotechnology, such as, for example, artificial gene synthesis, as polymerase chain reaction (PCR) primers, in DNA sequencing, and as molecular probes. In one embodiment, the oligonucleotides described herein may be used as primers for nucleic acid amplification or as probes for nucleic acid hybridization and detection. The terms "primer," "primer sequence," and "primer oligonucleotide," as used herein, refer to an oligonucleotide which is capable of acting as a point of initiation of synthesis of a primer extension product that is a complementary strand of nucleic acid (all types of DNA or RNA), when placed under suitable amplification conditions (e.g., buffer, salt, temperature and pH) in the presence of nucleotides and an agent for nucleic acid polymerization (e.g., a DNA-dependent or RNA-dependent polymerase). A primer can be single-stranded or double-stranded. If double-stranded, the primer may first be treated (e.g., denatured) to allow separation of its strands before being used to prepare extension products. Such a denaturation step is typically performed using heat, but may alternatively be carried out using alkali, followed by neutralization. The primers of the present disclosure can be of any suitable size, and desirably comprise, consist essentially of, or consist of about 15 to 50 nucleotides, preferably about 20 to 40 nucleotides, and more preferably about 22 to 30 nucleotides. The primers of the present disclosure can contain additional nucleotides in addition to those described herein. For example, depending on the type of amplification process employed, primers can include, for example, a restriction endonuclease recognition site 5' to the target binding sequence (see, e.g., U.S. Pat. Nos. 5,270,184 and 5,455,166), or an RNA polymerase promoter linked to the target binding sequence of the primer. A "forward primer" is a primer that hybridizes (or anneals) to a target nucleic acid sequence (e.g., template strand) for amplification. A "reverse primer" is a primer that hybridizes (or anneals) to the complementary strand of the target sequence during amplification. A forward primer hybridizes with a target sequence 5' with respect to a reverse primer.

The terms "probe," "probe sequence," and "probe oligonucleotide," refer to an oligonucleotide that can selectively hybridize to at least a portion of a target sequence under appropriate amplification conditions (e.g., a portion of a target sequence that has been amplified). In general, a probe sequence is identified as being either "complementary" (i.e., complementary to the coding or sense strand (+)), or "reverse complementary" (i.e., complementary to the antisense strand (−)). The probes of the present disclosure can be of any suitable size, and desirably comprise, consist essentially of, or consist of about 10-50 nucleotides, preferably about 12-35 nucleotides, and more preferably about 14-25 nucleotides.

As used herein, the terms "set," "primer set," "probe set," and "primer and probe set," refer to two or more oligonucleotide primers which together are capable of priming the amplification of a target sequence or target nucleic acid of interest (e.g., a target sequence within the HCV) and/or at least one probe which can detect the target sequence or target nucleic acid. In certain embodiments, the term "primer set" refers to a pair of primers including a forward primer (or 5' (upstream) primer) that hybridizes with the 5'-end of the target sequence or target nucleic acid to be amplified and a reverse primer (or 3' (downstream) primer) that hybridizes with the complement of the target sequence or target nucleic acid to be amplified. Such primer sets or primer pairs are particularly useful in PCR amplification reactions.

The set of oligonucleotides described herein may be used to amplify and detect a target HCV nucleic acid sequence in a sample. The terms "target sequence" and "target nucleic acid" are used interchangeably herein and refer to a specific nucleic acid sequence, the presence or absence of which is to be detected by the disclosed method. In the context of the present disclosure, a target sequence preferably includes a nucleic acid sequence to which one or more primers will hybridize and from which amplification will initiate. The target sequence can also include a probe-hybridizing region with which a probe may form a stable hybrid under appropriate amplification conditions. A target sequence may be single-stranded or double-stranded. The primer and probe sequences described herein can target any suitable nucleic acid sequence, or combination of sequences, present in the HCV genome. The HCV genome is a single-stranded positive sense RNA molecule approximately 9.5 kb in length, which codes for a single polyprotein, flanked by untranslated regions (UTRs) at both its 5' and 3' ends. (Clarke, B., *J. Gen. Virol.,* 78: 2397-410 (1997)). The 5' and 3' UTRs are not translated into proteins but are important for translation and replication of the viral RNA. In particular, the 5' UTR comprises a ribosome binding site that initiate translation of the HCV polyprotein. The core, E1, and E2 genes of HCV encode structural proteins, while the NS2, NS3, NS4A, NS4B, NS5A, and NS5B genes of HCV encode nonstructural proteins. The HCV polyprotein is cleaved by cellular and viral proteases into 10 smaller proteins, allowing for viral replication within the host cell and assembly into mature viral particles (Dubuisson, J., *World J. Gastroenterol,* 13(17): 2406-15 (2007)). At least six genotypes and more than 67 subtypes of HCV have been identified globally, which typically differ from each other by at least about 15% in coding regions (Echeverria et al., *World J. Hepatol.,* 7(6): 931-845 (2015)).

The set of oligonucleotides described herein may comprise, consist essentially of, or consist of any number of primer and probe oligonucleotides so as to amplify and detect any suitable number of HCV nucleic acid sequences. In one embodiment, the set of oligonucleotides described herein comprises, consists essentially of, or consists of two or more primers which amplify at least a portion of the 5' UTR of the HCV genome to produce a single HCV amplicon, and two or more probes which hybridize to two different regions of the single HCV amplicon. A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. As used herein, the term "amplicon" refers to a product of a natural or artificial amplification reaction. In other words, the set of oligonucleotides described herein comprise a "dual-probe"

design, in contrast to other commercially available HCV nucleic acid tests which utilize a single probe to detect and quantify HCV RNA (e.g., REALTIME™ HCV (Abbott Molecular, Inc., Des Plaines, Ill.); APTIMA® HCV Quant Dx (Hologic, Inc., Marlborough, Mass.); VERIS® HCV Assay (Beckman Coulter, Inc., Brea Calif.); and XPERT® HCV Viral Load Assay (Cepheid, Sunnyvale, Calif.)). In one embodiment, for example, the first target HCV nucleic acid sequence comprises a highly conserved nucleic acid sequence within the 5'UTR of HCV.

In one embodiment, the set of oligonucleotides described herein comprises, consists essentially of, or consists of (a) a forward primer oligonucleotide sequence comprising SEQ ID NO: 1 or SEQ ID NO: 5; (b) a reverse primer oligonucleotide sequence comprising SEQ ID NO: 2, SEQ ID NO: 6, SEQ ID NO: 7, SEQ ID NO: 8, or SEQ ID NO: 9; (c) a first probe oligonucleotide sequence comprising SEQ ID NO: 3, SEQ ID NO: 10, SEQ ID NO: 11, or SEQ ID NO: 12; and (d) a second probe oligonucleotide sequence comprising SEQ ID NO: 4, SEQ ID NO: 13, or SEQ ID NO: 14. For example, the set of oligonucleotides may comprise a forward primer oligonucleotide sequence comprising SEQ ID NO: 1; a reverse primer oligonucleotide sequence comprising SEQ ID NO: 2; a first probe oligonucleotide sequence comprising SEQ ID NO: 3; and a second probe oligonucleotide sequence comprising SEQ ID NO: 4 (also referred to as ALINITY m™ HCV).

Any one or combination of the oligonucleotides described herein may be modified in any suitable manner so as to stabilize or enhance the binding affinity (also referred to as "melting temperature" or "$T_m$") of a primer or probe oligonucleotide for its target. In this respect, an oligonucleotide sequence as described herein may comprise one or more modified oligonucleotide bases. For example, the oligonucleotide sequence may comprise one or more propyne-modified bases, wherein the oligonucleotide comprises an alkyne with the chemical formula $CH_3\equiv CCH$. The one or more propyne-modified bases may include, for example, 5-(1-propynyl)-2'-deoxy-Uridine (pdU) and/or 5-(1-propynyl)-2'-deoxyCytidine (pdC). In one embodiment, for example, a first oligonucleotide probe comprising the amino acid sequence of SEQ ID NO: 3 may comprise the propyne modified sequence of pdC-pdC-pdU-pdU-G-pdU-G-G-pdU-A-pdC-pdU-G-pdC-pdC-pdU-G (SEQ ID NO: 22).

Any one of the oligonucleotide sequences described herein may comprise, consist essentially of, or consist of a complement of any of the sequences disclosed herein. The terms "complement" or "complementary sequence," as used herein, refer to a nucleic acid sequence that forms a stable duplex with an oligonucleotide described herein via Watson-Crick base pairing rules, and typically shares about 80%, about 81%, about 82%, about 83%, about 84%, about 85%, about 86%, about 87%, about 88%, about 89%, about 90%, about 91%, about 92%, about 93%, about 94% about 95%, about 96%, about 97%, about 98% or about 99% greater identity with the disclosed oligonucleotide. Nucleic acid sequence identity can be determined using any suitable mathematical algorithm or computer software known in the art, such as, for example, CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.*, 215(3): 403-410 (1990); Beigert et al., *Proc. Natl. Acad. Sci. USA*, 106(10): 3770-3775 (2009), Durbin et al., eds., *Biological Sequence Analysis: Probalistic Models of Proteins and Nucleic Acids*, Cambridge University Press, Cambridge, UK (2009); Soding, *Bioinformatics*, 21(7): 951-960 (2005); Altschul et al., *Nucleic Acids Res.*, 25(17): 3389-3402 (1997); and Gusfield, *Algorithms on Strings, Trees and Sequences*, Cambridge University Press, Cambridge UK (1997)).

The oligonucleotides described herein may be prepared using any suitable method, a variety of which are known in the art (see, for example, Sambrook et al., *Molecular Cloning. A Laboratory Manual*, 1989, 2. Supp. Ed., Cold Spring Harbour Laboratory Press: New York, N.Y.; M. A. Innis (Ed.), *PCR Protocols. A Guide to Methods and Applications*, Academic Press: New York, N.Y. (1990); P. Tijssen, *Hybridization with Nucleic Acid Probes—Laboratory Techniques in Biochemistry and Molecular Biology (Parts I and II)*, Elsevier Science (1993); M. A. Innis (Ed.), *PCR Strategies*, Academic Press: New York, N.Y. (1995); and F. M. Ausubel (Ed.), Short Protocols in Molecular Biology, John Wiley & Sons: Secaucus, N.J. (2002); Narang et al., *Meth. Enzymol.*, 68: 90-98 (1979); Brown et al., *Meth. Enzymol.*, 68: 109-151 (1979); and Belousov et al., *Nucleic Acids Res.*, 25: 3440-3444 (1997)). Primer pairs also can be designed using a variety of tools, such as the Primer-BLAST tool provided by the National Center of Biotechnology Information (NCBI). Oligonucleotide synthesis may be performed on oligo synthesizers such as those commercially available from Perkin Elmer/Applied Biosystems, Inc. (Foster City, Calif.), DuPont (Wilmington, Del.), or Milligen (Bedford, Mass.). Alternatively, oligonucleotides can be custom made and obtained from a variety of commercial sources well-known in the art, including, for example, the Midland Certified Reagent Company (Midland, Tex.), Eurofins Scientific (Louisville, Ky.), BioSearch Technologies, Inc. (Novato, Calif.), and the like. Oligonucleotides may be purified using any suitable method known in the art, such as, for example, native acrylamide gel electrophoresis, anion-exchange HPLC (see, e.g., Pearson et al., *J. Chrom.*, 255: 137-149 (1983)), and reverse phase HPLC (see, e.g., McFarland et al., *Nucleic Acids Res.*, 7: 1067-1080 (1979)).

The sequence of the primers and probes can be verified using any suitable sequencing method known in the art, including, but not limited to, chemical degradation (see, e.g., Maxam et al., *Methods of Enzymology*, 65: 499-560 (1980)), matrix-assisted laser desorption ionization time-of-flight (MALDI-TOF) mass spectrometry (see, e.g., Pieles et al., *Nucleic Acids Res.*, 21: 3191-3196 (1993)), mass spectrometry following a combination of alkaline phosphatase and exonuclease digestions (Wu et al. *Anal. Biochem.*, 290: 347-352 (2001)), and the like.

The primer and probe oligonucleotides described herein desirably comprise a melting temperature ($T_M$) in the range 45° C. to 80° C. In accordance with the present disclosure, the oligonucleotides specifically hybridize to a target HCV nucleic acid sequence without exhibiting significant hybridization to non-HCV nucleic acids. In addition, the oligonucleotides are selected such that they hybridize to conserved regions in the HCV genome, thus minimizing mismatches with the target sequence. This selection ensures that the oligonucleotides are capable of hybridizing to HCV nucleic acids from all genotypes and subtypes. Furthermore, the oligonucleotides are selected such that they show the least likelihood of dimer formation and contain minimal sequence repeats. Such properties can be determined by methods known in the art, for example, using the computer modelling program OLIGO® Primer Analysis Software (distributed by National Biosciences, Inc., Plymouth, Minn.).

Detectable Label

Any one or more of the primer and probe oligonucleotide sequences described herein may comprise a detectable label, such that the primer and/or probe can be visualized, following binding to another entity (e.g., an amplification product or amplicon). The term "detectable label," as used herein, refers to a moiety or compound that generates a signal which can be measured and whose intensity is related to (e.g., proportional to) the amount of entity bound thereto. Any suitable detectable label that can be conjugated or linked to an oligonucleotide in order to detect binding of the oligonucleotide to a target sequence can be used, many of which are known in the art. In one embodiment, the detectable label may be detected indirectly. Indirectly detectable labels are typically specific binding members used in conjunction with a "conjugate" that is attached or coupled to a directly detectable label. Coupling chemistries for synthesizing such conjugates are well-known in the art and are designed such that the specific binding property of the specific binding member and the detectable property of the label remain intact. As used herein, "specific binding member" and "conjugate" refer to the two members of a binding pair, i.e. two different molecules, where the specific binding member binds specifically to the polynucleotide of the present disclosure, and the "conjugate" specifically binds to the specific binding member. Binding between the two members of the pair is typically chemical or physical in nature. Examples of such binding pairs include, but are not limited to, antigens and antibodies, avidin/streptavidin and biotin, haptens and antibodies specific for haptens, complementary nucleotide sequences, enzyme cofactors/substrates and enzymes, and the like.

In another embodiment, the detectable label may be directly detected. Such directly detectable labels include, for example, radioisotopes, fluorophores, chemiluminophores, enzymes, colloidal particles, fluorescent microparticles, intercalating dyes (e.g., SYBR Green or ethidium bromide), and the like. In one embodiment, the detectable label may be a fluorophore, such as a fluorescein-family dye, polyhalofluorescein-family dye, hexachlorofluorescein-family dye, coumarin-family dye, rhodamine-family dye, cyanine-family dye, oxazine-family dye, thiazin-family dye, squaraine-family dye, chelated lanthanide-family dye, azo-family dye, triphenylmethane-family dye, or a BODIPY®-family dye. Examples of fluorophores include, but are not limited to, FAM™, HEX™, JOE™, NED™, PET®, ROX™, TAMRA™, TET™, TEXAS RED®, and VIC®. One skilled in the art will appreciate that directly detectable labels may require additional components, such as substrates, triggering reagents, light, and the like, to enable detection of the label. Methods for labeling oligonucleotides, such as probes, are well-known in the art and described in, e.g., L. J. Kricka, *Ann. Clin. Biochem.*, 39: 114-129 (2002); van Gijlswijk et al., *Expert Rev. Mol. Diagn.*, 1: 81-91 (2001); Joos et al., *J. Biotechnol.*, 35: 135-153 (1994); Smith et al., *Nucl. Acids Res.*, 13: 2399-2412 (1985); Connoly et al., *Nucl. Acids. Res.*, 13: 4485-4502 (1985); Broker et al., *Nucl. Acids Res.*, 5: 363-384 (1978); Bayer et al., *Methods of Biochem. Analysis*, 26: 1-45 (1980); Langer et al., *Proc. Natl. Acad. Sci. USA*, 78: 6633-6637 (1981); Richardson et al., *Nucl. Acids Res.*, 11: 6167-6184 (1983); Brigati et al., *Virol.*, 126: 32-50 (1983); Tchen et al., *Proc. Natl. Acad. Sci. USA*, 81: 3466-3470 (1984); Landegent et al., *Exp. Cell Res.*, 15: 61-72 (1984); A. H. Hopman et al., *Exp. Cell Res.*, 169: 357-368 (1987); and Temsamani et al., *Mol. Biotechnol.*, 5: 223-232 (1996).

In another embodiment, any one or more of the primer and probe oligonucleotide sequences described herein may also comprise a quencher moiety. When a detectable label (e.g., a fluorophore) and quencher moiety are held in close proximity, such as at the ends of a probe, the quencher moiety prevents detection of a signal (e.g., fluorescence) from the detectable label. When the two moieties are physically separated, such as after cleavage by a DNA polymerase, the signal becomes detectable. The quencher may be selected from any suitable quencher known in the art, such as, for example, BLACK HOLE QUENCHER® 1 (BHQ-1®), BLACK HOLE QUENCHER® 2 (BHQ-2®), IOWA BLACK® FQ, and IOWA BLACK® RQ. For example, the oligonucleotide probe may comprise a FAM fluorophore and a BHQ-1 quencher.

Both the first and second probe oligonucleotide sequences desirably comprise a detectable label. Each of the probes may be labeled with the same detectable label or different detectable labels. When both probes comprise the same detectable label (e.g., FAM), amplification of the HCV target sequence is detected as a single signal during real-time PCR. When each probe comprises a different detectable label, amplification of the HCV target sequence is detected as two separate signals.

The selection of a particular labeling technique will depend on several factors, such as the ease and cost of the labeling method, spectral spacing between different detectable labels used, the quality of sample labeling desired, the effects of the detectable moiety on the hybridization reaction (e.g., on the rate and/or efficiency of the hybridization process), the nature of the amplification method used, the nature of the detection system, the nature and intensity of the signal generated by the detectable label, and the like.

Internal Control

The set of oligonucleotides for detecting HCV described above may further comprise primer and probe oligonucleotide sequences for amplifying and detecting an internal control (IC) sequence. In one embodiment, the internal control sequences are added to each sample preparation reaction. The internal control is then processed through the entire sample preparation and amplification procedure along with the test samples and calibrators (if present), to demonstrate proper sample processing and assay validity. The internal control may be any suitable non-HCV nucleic acid sequence, including, for example, a nucleic acid sequence encoding GAPDH, beta2-mciroglobulin, beta-actin, R18, or 16S RNA. In some embodiments, the internal control desirably comprises, consists essentially of, or consists of an armored RNA target sequence. The term "armored RNA," as used herein, refers to RNase-resistant RNA that is a complex of MS2 bacteriophage coat protein and RNA produced in *Escherichia coli* by the induction of an expression plasmid that encodes the coat protein and an RNA standard sequence (see, e.g., Pasloske et al., *J. Clin. Microbiol.*, 36(12): 3590-359 (1998); and U.S. Pat. Nos. 5,677,124, 5,919,625, and 5,939,262). In one embodiment, for example, the internal control may comprise an RNA sequence derived or obtained from the hydroxypyruvate reductase gene of the pumpkin plant, *Curcurbita pepo*. In this regard, the set of oligonucleotides described herein may further comprise an internal control forward primer oligonucleotide sequence comprising SEQ ID NO: 15, an internal control reverse primer oligonucleotide sequence comprising SEQ ID NO: 16, and an internal control probe oligonucleotide sequence comprising SEQ ID NO: 17. The internal control probe desirably comprises a detectable label, such as any of those described herein. In one embodiment, the internal control probe may comprise a different label than the probes used to detect HCV, which allows for simultaneous detection and differentiation of internal control and HCV-amplified products within the same reaction. The internal control probe may also comprise a quencher moiety, such as those described herein.

Method for Amplifying and Detecting Human Hepatitis C Virus

The present disclosure provides a method for detecting human hepatitis C virus (HCV) in a sample suspected of containing HCV. The method comprises: (a) contacting a sample obtained from a human with the set of oligonucleotide sequences described herein and reagents for amplification and detection of nucleic acid sequences, (b) amplifying a first target HCV nucleic acid sequence present in the sample, (c) hybridizing the first and second oligonucleotide probes to the first target HCV nucleic acid sequence, (d) detecting hybridization of the first and second probe oligonucleotide sequences to the first target HCV nucleic acid sequence by assessing a signal from each of the detectable labels, whereby (i) the presence of the signals indicates hybridization of the first and second probe oligonucleotide sequences to the first target HCV nucleic acid sequence and the presence of HCV in the sample, and (ii) the absence of the signals indicates the absence of HCV in the sample. Descriptions of the primer and probe oligonucleotides set forth herein with respect to the aforementioned set of oligonucleotides also are applicable to those same aspects of the disclosed method.

A sample, as defined herein, is "suspected" of containing HCV if the sample is obtained from a subject, preferably a human, suspected of being infected with HCV. A subject is suspected of being infected with HCV if the subject has an increased risk for HCV. The most common mode of HCV transmission in the United States is through injection drug use. Other groups at higher risk for HCV infection include, for example, past injection drug users, recipients of donated blood, blood products, and organs, individuals who received a blood product for clotting problems made before 1987, hemodialysis patients or persons who spent multiple years on dialysis for kidney failure, people who received body piercing or tattoos with non-sterile instruments, people with known exposures to the Hepatitis C virus (e.g., health care workers injured by needlesticks and recipients of blood or organs from a donor who tested positive for the Hepatitis C virus), HIV-infected persons, and children born to mothers infected with HCV.

The sample can be any suitable sample obtained from any suitable subject, typically a mammal (e.g., dogs, cats, rabbits, mice, rats, goats, sheep, cows, pigs, horses, non-human primates, or humans). Preferably, the subject is a human. The sample may be obtained from any biological source, such as, a cervical, vaginal or anal swab or brush, or a physiological fluid including, but not limited to, whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and the like. The sample can be obtained from the subject using routine techniques known to those skilled in the art, and the sample may be used directly as obtained from the biological source or following a pretreatment to modify the character of the sample. Such pretreatment may include, for example, preparing plasma from blood, diluting viscous fluids, filtration, precipitation, dilution, distillation, mixing, concentration, inactivation of interfering components, the addition of reagents, lysing, etc.

After the sample is obtained from a subject, the sample may be contacted with the set of oligonucleotides comprising forward and reverse primers and first and second probes as described herein to form a reaction mixture. The reaction mixture is then placed under amplification conditions. The primers hybridize to a first target HCV nucleic acid sequence (e.g., a region of the 5'UTR of the HCV genome) if present in the sample, and the a first target HCV nucleic acid sequence present in the sample is amplified.

Amplifying an HCV nucleic acid sequence in the sample can be performed using any suitable nucleic acid sequence amplification method known in the art, including but not limited to, polymerase chain reaction (PCR), reverse-transcriptase PCR (RT-PCR), real-time PCR, transcription-mediated amplification (TMA), rolling circle amplification, nucleic acid sequence based amplification (NASBA), strand displacement amplification (SDA), and ligase chain reaction (LCR).

Because HCV comprises an RNA genome, amplification of the HCV virus nucleic acid sequence desirably is performed using RT-PCR, and preferably real-time RT-PCR. "RT-PCR," as used herein, refers to the enzymatic reaction in which complimentary DNA (cDNA) fragments are synthesized from a substrate RNA template. The reaction typically involves the use of a synthetic oligonucleotide primer, which is complementary to nucleotide sequences in the substrate RNA, and the use of a reverse transcriptase enzyme. The reaction consists of one cycle, in which the oligonucleotide primers, which are present in vast excess, hybridize to the substrate RNA to form double-stranded structures along complementary nucleotide sequences. The primer-substrate DNA:RNA complexes will then serve as initiation sites for a cDNA synthesis reaction catalyzed by reverse transcriptase, resulting in the synthesis of a cDNA strand complementary to the RNA strand. The RNA may be a messenger RNA (mRNA), transfer RNA (tRNA), genomic RNA (gRNA), ribosomal RNA (rRNA), or a small nuclear RNA (snRNA). Methods and reagents for RT-PCR well known in the art and commercially available from a variety of sources (see, e.g., Freeman et al., *Biotechniques*, 26(1): 112-122, 142-125 (1999); Joyce, C., *Methods Mol. Biol.*, 193: 83-92 (2002); and O'Connell, J. (ed.), *RT-PCR Protocols*, 1st Ed., Springer-Verlag, New York, N.Y. (2010)). Reverse transcription can be performed using one-step or two-step techniques known in the art, such as, for example, by using reverse transcription kits available from Thermo Fisher Scientific (Waltham, Mass.) Qiagen (Hilden, Germany), and Promega Corp. (Madison, Wis.).

"Real-time PCR," as used herein, refers to a PCR method in which the accumulation of amplification product is measured as the reaction progresses, in real time, with product quantification after each cycle, in contrast to conventional PCR in which the amplified DNA product is detected in an end-point analysis. Real-time PCR also is known in the art at "quantitative PCR (qPCR)." Real-time detection of PCR products typically involves the use of non-specific fluorescent dyes that intercalate with any double-stranded DNA and sequence-specific fluorescently-labeled DNA probes. Real-time PCR techniques and systems are known in the art (see, e.g., Dorak, M. Tevfik, ed. *Real-time PCR*. Taylor & Francis (2007); and Fraga et al., "Real-time PCR," *Current protocols essential laboratory techniques:* 10-3 (2008)) and are commercially available from a variety of sources (e.g., m2000rt REALTIME™ PCR system (Abbott Molecular, Inc., Des Plaines, Ill.); CFX Real-Time PCR Detection Systems (Bio-Rad Laboratories, Inc., Hercules, Calif.); and TAQMAN™ Real-Time PCR System (ThermoFisher Scientific, Waltham, Mass.)), any of which can be employed in the methods described herein.

Following amplification of an HCV virus nucleic acid sequence (e.g., a region of the HCV 5' UTR) that is present in the sample, the disclosed method further comprises hybridizing the first and second probe oligonucleotides to the first target HCV nucleic acid sequence. In one embodiment, a reaction mixture comprising an HCV amplicon may be contacted with the first and second oligonucleotide probes, as described herein, that preferentially hybridize to a target nucleic acid sequence of the amplicon, or the complement thereof, under stringent hybridization and wash conditions, thereby forming a hybrid duplex that is stable for detection.

"Hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. "Stringent hybridization conditions" as used herein means conditions under which hybridization of fully complementary nucleic acid strands is strongly preferred. Under stringent hybridization conditions, a first nucleic acid sequence (for example, a primer) will hybridize to a second nucleic acid sequence (for example, a target sequence), such as in a complex mixture of nucleic acids. Stringent conditions are sequence-dependent and will be different in different circumstances. Stringent conditions can be selected to be about 5-10° C. lower than the thermal melting point ($T_m$) for the specific sequence at a defined ionic strength pH. The $T_m$ can be the temperature (under defined ionic strength, pH, and nucleic concentration) at which 50% of an oligonucleotide complementary to a target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5× SSC, and 1% SDS, incubating at 42° C., or, 5× SSC, 1% SDS, incubating at 65° C., with wash in 0.2× SSC, and 0.1% SDS at 65° C. Any suitable method and conditions for hybridizing the first and second oligonucleotide probes to the first target HCV nucleic acid sequence known in the art can be used in the disclosed method.

Following hybridization of the first and second probe oligonucleotide sequences to the first target HCV nucleic acid sequence, the method comprises detecting hybridization of the first and second probe oligonucleotide sequences to the first target HCV nucleic acid sequence by assessing a signal from each of the detectable labels, whereby (i) the presence of the signals indicates hybridization of the first and second probe oligonucleotide sequences to the first target HCV nucleic acid sequence and the presence of HCV in the sample, and (ii) the absence of the signals indicates the absence of HCV in the sample. Detection of signals from the first and second probes may be performed using a variety of well-known methodologies, including, for example homogeneous or heterogeneous techniques.

Homogeneous detection methods involve detecting products of the amplification reaction as they are formed, namely, in a real time manner. As a result, amplification product/probe hybrids are formed and detected while the reaction mixture is under amplification conditions. Homogeneous detection methods include, but are not limited to, the use of FRET labels that are attached to the probes and that emit a signal in the presence of the target sequence, Molecular Beacons (See, Tyagi et al., *Nature Biotechnol.*, 14: 303-308 (1996); Tyagi et al., *Nature Biotechnol.*, 16: 49-53 (1998); Kostrikis et al., *Science*, 279: 1228-1229 (1998); Sokol et al., *Proc. Natl. Acad. Sci. USA*, 95: 11538-11543 (1998); Marras et al., *Genet. Anal.*, 14: 151-156 (1999); and U.S. Pat. Nos. 5,846,726, 5,925,517, 6,277,581 and 6,235,504), TAQMAN® assays (see, e.g., U.S. Pat. Nos. 5,210,015; 5,804,375; 5,487,792 and 6,214,979 and International Patent Application Publication WO 01/86001), and hybridization protection assays (HPA) which utilize probes labeled with acridinium ester (AE) (see, e.g., Weeks et al., *Clin. Chem.*, 29: 1474-1479 (1983); Berry et al., *Clin. Chem.*, 34: 2087-2090 (1988)).

Heterogeneous detection systems generally employ a capture agent to separate amplified sequences from other materials in the reaction mixture. Capture agents typically comprise a solid support material (e.g., microtiter wells, beads, chips, and the like) coated with one or more specific binding sequences. A binding sequence may be complementary to a tail sequence added to oligonucleotide probes of the disclosure. Alternatively, a binding sequence may be complementary to a sequence of a capture oligonucleotide, itself comprising a sequence complementary to a tail sequence of a probe. After separation of the amplification product/probe hybrids bound to the capture agents from the remaining reaction mixture, the amplification product/probe hybrids can be detected using any suitable detection method known in the art or described herein.

In another embodiment, the method of detecting HCV in a sample may further comprise contacting the sample with a primer and probe set that amplifies and detects a second target HCV nucleic acid sequence in the sample. The second target HCV nucleic acid sequence may be any HCV protein-coding sequence described herein, or a portion thereof. In one embodiment, the second target HCV nucleic acid sequence is located within the 3' UTR of the HCV genome. As discussed above, the HCV 3' UTR is not translated into protein but is important for translation and replication of the viral RNA. In particular, the 3' UTR has been shown to retain ribosome complexes during translation termination to facilitate efficient initiation of subsequent rounds of translation (see, e.g., Bai et al., *Nucleic Acids Res.*, 41(16): 7861-7874 (2013)), and may be involved in virus encapsidation (see, e.g., Shi et al., *PLoS Pathog.*, 12(2): e1005441 (2016)). The second target HCV nucleic acid sequence desirably comprises at least a portion of the 3' untranslated region (UTR) of the HCV genome. In one embodiment, the primer and probe set that amplifies and detects a second target HCV nucleic acid sequence in the sample comprises (a) a forward primer oligonucleotide sequence comprising SEQ ID NO: 18; (b) a reverse primer oligonucleotide sequence comprising SEQ ID NO: 19; and (c) a probe oligonucleotide sequence comprising SEQ ID NO: 20 or SEQ ID NO: 21 and a detectable label.

Kits and Compositions for Amplifying and Detecting a Hepatitis C Virus Nucleic Acid Sequence The disclosure also provides a kit for amplifying and detecting human HCV in a sample. The kit comprises a forward primer oligonucleotide, a reverse primer oligonucleotide, a first probe oligonucleotide comprising a detectable label, a second probe oligonucleotide comprising a detectable label, and reagents and instructions for amplifying and detecting HCV. Descriptions of the primer oligonucleotides and probe oligonucleotides set forth herein with respect to the aforementioned methods also are applicable to those same aspects of the kits described herein. Examples of suitable reagents for inclusion in the kit (in addition to the oligonucleotide primers and probes described herein) include conventional reagents employed in nucleic acid amplification reactions, such as, for example, one or more enzymes having polymerase activity, enzyme cofactors (such as magnesium or nicotinamide adenine dinucleotide (NAD)), salts, buffers, deoxyribonucleotide, or ribonucleotide triphosphates (dNTPs/rNTPs; for example, deoxyadenosine triphosphate, deoxyguanosine triphosphate, deoxycytidine triphosphate, and deoxythymidine triphosphate) blocking agents, labeling agents, and the like. Many such reagents are described herein or otherwise known in the art and commercially available.

In one embodiment, the kit may comprise, consist essentially of, or consist of (a) a forward primer oligonucleotide sequence comprising SEQ ID NO: 1; (b) a reverse primer oligonucleotide sequence comprising SEQ ID NO: 2; (c) a first probe oligonucleotide sequence comprising SEQ ID NO: 3; (d) a second probe oligonucleotide sequence comprising SEQ ID NO: 4; (e) reagents for amplifying and detecting nucleic acid sequences; and (f) instructions for use, wherein each of the first and second probes comprises a detectable label. In another embodiment, the kit may comprise (a) a forward primer oligonucleotide sequence comprising SEQ ID NO: 5, (b) a reverse primer oligonucleotide sequence comprising SEQ ID NO: 6, SEQ ID NO: 7, SEQ ID NO: 8, or SEQ ID NO: 9, (c) a first probe oligonucleotide sequence comprising SEQ ID NO: 10, SEQ ID NO: 11, or SEQ ID NO: 12, (d) a second probe oligonucleotide sequence comprising SEQ ID NO: 13 or SEQ ID NO: 14, (e) reagents for amplifying and detecting nucleic acid sequences; and (f) instructions for use, wherein each of the first and second probes comprises a detectable label.

The kit may comprise instructions for using the amplification reagents and primer and probe oligonucleotides described herein, e.g., for processing the test sample, extracting nucleic acid molecules, and/or performing the test; and for interpreting the results obtained, as well as a notice in the form prescribed by a governmental agency. Such instructions optionally can be in printed form or on CD, DVD, or other format of recorded media.

The present disclosure also provides a composition for amplifying and detecting HCV in a sample. The composition comprises, consists essentially of, or consists of a forward primer oligonucleotide, a reverse primer oligonucleotide, a first probe oligonucleotide comprising a detectable label, and a second probe oligonucleotide comprising a detectable label. Descriptions of the primer oligonucleotides and probe oligonucleotides set forth herein with respect to the aforementioned methods and kit also are applicable to those same aspects of the composition described herein. In some embodiments, the composition comprises a carrier, preferably a pharmaceutically (e.g., physiologically acceptable) carrier. Any suitable carrier can be used within the context of the disclosure, and such carriers are well known in the art.

The composition can optionally be sterile or sterile with the exception of the oligonucleotides described herein.

The aforementioned kit and composition may further comprise primer and probe oligonucleotides that amplify and detect an internal control nucleic acid sequence, as described herein. In this regard, the kit and/or composition may comprise an internal control forward primer oligonucleotide sequence comprising SEQ ID NO: 15, an internal control reverse primer oligonucleotide sequence comprising SEQ ID NO: 16, and an internal control probe oligonucleotide sequence comprising SEQ ID NO: 17 which comprises a detectable label. In another embodiment, the aforementioned kit and composition may comprise an additional primer and probe set that amplifies and detects at least a portion of the 3' UTR of the HCV genome. In particular, for example, the kit and/or compositions may comprise a forward primer oligonucleotide sequence comprising SEQ ID NO: 18; a reverse primer oligonucleotide sequence comprising SEQ ID NO: 19; and a probe oligonucleotide sequence comprising SEQ ID NO: 20 or SEQ ID NO: 21 and a detectable label.

The kits and/or composition may be supplied in a solid (e.g., lyophilized) or liquid form. In one embodiment, the primer oligonucleotides, probe oligonucleotides, and other reagents are lyophilized (i.e., freeze dried). The various components of the kits and composition of the present disclosure may optionally be contained within different containers (e.g., vial, ampoule, test tube, flask, or bottle) for each individual component (e.g., primer oligonucleotides, probe oligonucleotides, or buffer). Each component will generally be suitable as aliquoted in its respective container or provided in a concentrated form. Other containers suitable for conducting certain steps of the amplification/detection assay may also be provided. The individual containers are preferably maintained in close confinement for commercial sale.

The following example further illustrates the invention but, of course, should not be construed as in any way limiting its scope.

EXAMPLE

This example demonstrates a method for amplifying and detecting human HCV in a sample in accordance with the present disclosure.

An HCV detection assay that utilizes real-time RT-PCR to amplify and detect HCV RNA genomic sequences extracted from human plasma or serum specimens has been developed by Abbott Molecular, Inc. (Des Plaines, Ill.) under the brand name ALINITY m™ HCV. The assay is intended to be used (1) to assess disease prognosis by measuring the baseline HCV level and to assess viral response to antiretroviral treatment by measuring changes of HCV RNA levels in serum or plasma; and (2) as an aid in the diagnosis of HCV infection and to confirm HCV infection in plasma or serum from individuals that have reactive results with HCV immunoassays.

The ALINITY m™ HCV assay consists of sample preparation, RT-PCR assembly, amplification/detection, and result calculation and reporting. All stages of the ALINITY m™ HCV assay procedure are executed automatically by the ALINITY m™ instrument. HCV RNA from human plasma or serum is extracted automatically on-board the Abbott ALINITY m™ instrument using the ALINITY m™ RNA Sample Prep Kit, ALINITY m™ Lysis Solution, and ALIN- ITY m™ Diluent Solution, which employ magnetic microparticle technology to facilitate nucleic acid capture, wash, and elution.

At the beginning of the ALINITY m™ HCV sample preparation process, a lyophilized unit-dose of internal control (containing an armored RNA sequence) is automatically rehydrated by the ALINITY m™ system and delivered into each sample preparation reaction. The internal control is then processed through the entire sample preparation and RT-PCR procedure along with the specimens, calibrators, and controls to demonstrate proper sample processing and assay validity. The internal control target is prepared by mixing excipient (trehalose and Molecular Biology Grade Water) and internal control bulk (consisting of internal control armored RNA diluted in filtered, defibrinated human plasma (Basematrix, SeraCare Life Science, Inc., Milford, Mass.). The formulation of the internal control is set forth in Table 1 below. The internal control armored RNA target sequence is derived from the hydroxypyruvate reductase gene of the pumpkin plant, *Cucurbita pepo*, which is unrelated to HCV. The internal control is filled in unit-dose format into multi-well plates and lyophilized. The lyophilized plates are then sealed and pouched.

TABLE 1

Internal Control Formulation

| Component | Component Concentration (pre-lyophilization) |
|---|---|
| Internal Control Armored RNA | Ct Target = 20.6 |
| Base Matrix with Internal Control Armored RNA | 50% |
| Molecular Biology Grade Water with 7.50% Trehalose | 50% |

25 µL of the purified RNA sample is then combined with 5 µL of liquid activator, which is then used to rehydrate lyophilized unit dose ALINITY m™ HCV RT-PCR master mix reagent. The activator solution is prepared by mixing molecular biology grade water, magnesium chloride, and tetramethyl ammonium chloride (TMAC). The activator solution is supplied in liquid format in sealed and pouched multi-well plates, and provides the RT-PCR reaction with the necessary salts to activate RT-PCR enzymes and establish an optimal ionic strength environment. The formulation of the activator solution is shown in Table 2.

TABLE 2

Activator Reagent Formulation

| Component | Component Concentration (in 30 µL PCR) |
|---|---|
| Magnesium Chloride (MgCl$_2$) | 6 mM |
| Tetramethyl Ammonium Chloride (TMAC) | 90 mM |
| ProClin 950 | 0.025% |
| Molecular Biology Grade Water | N/A |

The resulting material is then transferred to a reaction vessel, covered with 15 µL of ALINITY m™ Vapor Barrier Solution (mineral oil), and transferred to an amplification/detection module for reverse transcription, PCR amplification, and real-time fluorescence detection of HCV.

The RT-PCR master mix reagent formulation is compatible with lyophilization and enables completion of RT-PCR cycling in less than one hour. The master mix reagent is prepared by combining KAPA 2G DNA Polymerase, SuperScript III Reverse Transcriptase, Uracil-DNA Glycosylase (UDG), excipient (Ficoll 400, Ficoll 70, trehalose, melezitose and Molecular Biology Grade Water), PCR buffer components (Tris-HCl, Tween 20, and gelatin), dNTPs, forward and reverse oligonucleotide primers (as described herein), two oligonucleotide probes (as described herein), Cal610 passive reference dye, and ProClin 950.

SuperScript III Reverse Transcriptase is an engineered version of Moloney Murine Leukemia Virus (M-MLV) reverse transcriptase with reduced RNase H activity and increased thermal stability, and it can be used to synthesize first-strand cDNA at temperatures up to 55° C., providing increased specificity. KAPA2G Polymerase is an engineered enzyme for higher processivity and speed through directed evolution, which offers significantly faster extension rates than wild-type TAQ® DNA polymerase. KAPA2G has a highly processive 5'-3' DNA polymerase but lacks 3'-5' exonuclease activity. Uracil-DNA Glycosylase (UDG) catalyzes the release of free uracil from uracil-containing DNA and provides a means of contamination control for external amplicons containing uracil.

The master mix reagent is filled in unit-dose format into multi-well plates and lyophilized. The lyophilized plates are then sealed and pouched. The master mix formulation is set forth in Table 3.

TABLE 3

Master Mix Formulation

| Master Mix Component | Component Concentration (in 30 µL PCR) |
|---|---|
| HCV PCR Fwd Primer | 0.1 µM |
| HCV PCR Rev Primer | 1.0 µM |
| HCV mC Probe | 0.3 µM |
| HCV Cb Probe | 0.03 µM |
| IC Fwd Primer 196 | 0.1 µM |
| IC Rev Primer 310 | 0.2 µM |
| HCV GT IC Probe | 0.1 µM |
| Cal610 | 0.025 µM |
| dNTPs | 0.7 mM |
| Tris-HCl | 50 mM |
| Tween 20 | 0.010% (V/V) |
| Gelatin | 0.010% (W/V) |
| Fast Enzyme (KAPA 2G) | 1.8 units/reaction |
| Superscript III Reverse Transcriptase | 9 units/reaction |
| Uracil-DNA Glycosylase | 0.25 units/reaction |
| Ficoll 400 | 1.81% (W/V) |
| Ficoll 70 | 1.81% (W/V) |
| Melezitose | 0.60% (W/V) |
| Trehalose | 1.81% (W/V) |
| Molecular Biology Grade Water | N/A |

The RT-PCR cycling conditions used by the ALINITY m™ HCV assay are set forth in Table 4.

TABLE 4

RT-PCR Cycling Conditions

| Step | Description | Cycles | Temp. (C. °) | Dwell (sec.) | Ramp Rate (C. °/sec) |
|---|---|---|---|---|---|
| 1 | Reverse Transcription | 1 | 53 | 1045.01 | 10 |
| 2 | Hot Start | 1 | 95 | 180 | 10 |
| 3 | High Stringency Amplification (no read) | 4 | 97 | 3.2 | 10 |
|  |  |  | 63 | 20 | 8 |
| 4 | High Stringency Amplification (no read) | 3 | 97 | 3.2 | 10 |
|  |  |  | 60 | 5 | 8 |

TABLE 4-continued

RT-PCR Cycling Conditions

| Step | Description | Cycles | Temp. (C. °) | Dwell (sec.) | Ramp Rate (C. °/sec) |
|---|---|---|---|---|---|
| 5 | Amplification/Read | 38 | 97 | 3.2 | 10 |
|   |   |   | 60 | 23.67 | 8 |

The PCR formulation and cycling conditions described above may be further modified to optimize the assay.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. The phrase "consisting essentially of" also is construed to be an open-ended phrase meant to include steps or materials which do not materially affect the basic and novel characteristics of a described product or method. The phrase "consisting of" is construed to be a closed phrase which excludes any element, step, or ingredient not explicitly specified in the specification or claims. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A set of oligonucleotide sequences for amplifying and detecting a human hepatitis C virus (HCV) nucleic acid sequence in a sample, which comprises:
   (a) a forward primer oligonucleotide sequence comprising SEQ ID NO: 1 or SEQ ID NO: 5;
   (b) a reverse primer oligonucleotide sequence comprising SEQ ID NO: 2, SEQ ID NO: 6, SEQ ID NO: 7, SEQ ID NO: 8, or SEQ ID NO: 9;
   (c) a first probe oligonucleotide sequence comprising SEQ ID NO: 3, SEQ ID NO: 10, SEQ ID NO: 11, or SEQ ID NO: 12; and
   (d) a second probe oligonucleotide sequence comprising SEQ ID NO: 4, SEQ ID NO: 13, or SEQ ID NO: 14, wherein each of the first and second probe oligonucleotide sequences comprises a detectable label.

2. The set of claim 1, further comprising:
   (e) an internal control forward primer oligonucleotide sequence comprising SEQ ID NO: 15,
   (f) an internal control reverse primer oligonucleotide sequence comprising SEQ ID NO: 16, and
   (g) an internal control probe oligonucleotide sequence comprising SEQ ID NO: 17 and a detectable label.

3. The set of claim 1, wherein:
   (a) the forward primer oligonucleotide sequence comprises SEQ ID NO: 1;
   (b) the reverse primer oligonucleotide sequence comprises SEQ ID NO: 2;
   (c) the first probe oligonucleotide sequence comprises SEQ ID NO: 3; and
   (d) the second probe oligonucleotide sequence comprises SEQ ID NO: 4.

4. The set of claim 1, wherein the detectable label is a fluorophore.

5. The set of claim 1, wherein each of the probe oligonucleotides further comprises a quencher moiety.

6. A method for detecting human hepatitis C virus (HCV) in a sample suspected of containing HCV, which method comprises:
   (a) contacting a sample obtained from a human with the set of oligonucleotide sequences of claim 1 and reagents for amplification and detection of nucleic acid sequences,
   (b) amplifying a first target HCV nucleic acid sequence present in the sample,
   (c) hybridizing the first and second oligonucleotide probes to the first target HCV nucleic acid sequence,
   (d) detecting hybridization of the first and second probe oligonucleotide sequences to the first target HCV nucleic acid sequence by assessing a signal from each of the detectable labels, whereby
      (i) the presence of the signals indicates hybridization of the first and second probe oligonucleotide sequences to the first target HCV nucleic acid sequence and the presence of HCV in the sample, and
      (ii) the absence of the signals indicates the absence of HCV in the sample.

7. The method of claim 6, wherein the first target HCV nucleic acid sequence comprises at least a portion of the 5' untranslated region (UTR) of the HCV genome.

8. The method of claim 6, which further comprises contacting the sample with a primer and probe set that amplifies and detects a second target HCV nucleic acid sequence.

9. The method of claim 8, wherein the second target HCV nucleic acid sequence comprises at least a portion of the 3' untranslated region (UTR) of the HCV genome.

10. The method of claim 8, wherein the primer and probe set comprises:
   (a) a forward primer oligonucleotide sequence comprising SEQ ID NO: 18;
   (b) a reverse primer oligonucleotide sequence comprising SEQ ID NO: 19; and
   (c) a probe oligonucleotide sequence comprising SEQ ID NO: 20 or SEQ ID NO: 21 and a detectable label.

11. The method of claim 6, wherein the sample comprises blood, serum, plasma, saliva, urine, vaginal fluid, or semen.

12. A kit for detecting human hepatitis C virus (HCV) in a sample comprising
   (a) a forward primer oligonucleotide sequence comprising SEQ ID NO: 1;
   (b) a reverse primer oligonucleotide sequence comprising SEQ ID NO: 2;
   (c) a first probe oligonucleotide sequence comprising SEQ ID NO: 3;
   (d) a second probe oligonucleotide sequence comprising SEQ ID NO: 4;
   (e) reagents for amplifying and detecting nucleic acid sequences; and
   (f) instructions for use,
   wherein each of the first and second probe oligonucleotide sequences comprises a detectable label.

13. The kit of claim 12, which further comprises:
   (g) an internal control forward primer oligonucleotide sequence comprising SEQ ID NO: 15,
   (h) an internal control reverse primer oligonucleotide sequence comprising SEQ ID NO: 16, and
   (i) an internal control probe oligonucleotide sequence comprising SEQ ID NO: 17 and a detectable label.

14. The kit of claim 12, which further comprises a primer and probe set that amplifies and detects at least a portion of the 3' untranslated region (UTR) of the HCV genome.

15. The kit of claim 14, wherein the primer and probe set comprises:
   (a) a forward primer oligonucleotide sequence comprising SEQ ID NO: 18;
   (b) a reverse primer oligonucleotide sequence comprising SEQ ID NO: 19; and
   (c) a probe oligonucleotide sequence comprising SEQ ID NO: 20 or SEQ ID NO: 21 and a detectable label.

16. The kit of claim 12, wherein the primers, probes, and reagents are lyophilized.

17. A composition for amplifying and detecting a human hepatitis C virus (HCV) in a sample, which comprises:
   (a) a forward primer oligonucleotide sequence comprising SEQ ID NO: 1 or SEQ ID NO: 5;
   (b) a reverse primer oligonucleotide sequence comprising SEQ ID NO: 2, SEQ ID NO: 6, SEQ ID NO: 7, SEQ ID NO: 8, or SEQ ID NO: 9;
   (c) a first probe oligonucleotide sequence comprising SEQ ID NO: 3, SEQ ID NO: 10, SEQ ID NO: 11, or SEQ ID NO: 12; and
   (d) a second probe oligonucleotide sequence comprising SEQ ID NO: 4, SEQ ID NO: 13, or SEQ ID NO: 14, wherein each of the first and second probe oligonucleotide sequences comprises a detectable label.

18. The composition of claim 17, which further comprises:
   (a) a forward primer oligonucleotide sequence comprising SEQ ID NO: 18;
   (b) a reverse primer oligonucleotide sequence comprising SEQ ID NO: 19; and
   (c) a probe oligonucleotide sequence comprising SEQ ID NO: 20 or SEQ ID NO: 21 and a detectable label.

19. The composition of claim 17, wherein the primer oligonucleotides, probe oligonucleotides, and reagents are lyophilized.

* * * * *